US012635821B1

(12) United States Patent
Pu

(10) Patent No.: US 12,635,821 B1
(45) Date of Patent: May 26, 2026

(54) GLOVE DONNING AID MACHINE

(71) Applicant: Zhuojun Pu, Guangzhou (CN)

(72) Inventor: Zhuojun Pu, Guangzhou (CN)

(73) Assignee: Pu Zhuojun, Guangzhou (CN)

( * ) Notice: Subject to any disclaimer, the term of this patent is extended or adjusted under 35 U.S.C. 154(b) by 0 days.

(21) Appl. No.: 19/218,446

(22) Filed: May 26, 2025

(51) Int. Cl.
*A47G 25/90* (2006.01)
*A61B 42/50* (2016.01)

(52) U.S. Cl.
CPC ............ *A47G 25/904* (2013.01); *A61B 42/50* (2016.02)

(58) Field of Classification Search
CPC ........ A47G 25/904; A61B 42/40; A61B 42/50
See application file for complete search history.

(56) References Cited

U.S. PATENT DOCUMENTS

| | | | | |
|---|---|---|---|---|
| 5,878,909 | A * | 3/1999 | Rogow | A61B 42/50 |
| | | | | 221/45 |
| 6,932,253 | B2 * | 8/2005 | Sato | A47G 25/904 |
| | | | | 223/111 |
| 6,953,130 | B2 * | 10/2005 | Corbett | A47G 25/904 |
| | | | | 221/33 |
| 8,807,402 | B2 * | 8/2014 | Backhaus | A41D 19/0072 |
| | | | | 223/111 |
| 8,855,810 | B2 * | 10/2014 | Chuah | B25J 9/1697 |
| | | | | 414/730 |
| 10,143,528 | B2 * | 12/2018 | Gaines | A47G 25/904 |
| 10,610,319 | B2 * | 4/2020 | Backhaus | A47G 25/904 |
| 11,330,925 | B2 * | 5/2022 | Löfholm | A61B 42/50 |

| | | | | |
|---|---|---|---|---|
| 11,617,629 | B2 * | 4/2023 | Shalom Avshalom | A61B 42/50 |
| | | | | 223/111 |
| 11,889,936 | B2 * | 2/2024 | Waineo | A47G 25/904 |
| 12,114,795 | B2 * | 10/2024 | Sher | B25J 9/0084 |
| 12,414,658 | B2 * | 9/2025 | Dally | A61B 42/40 |
| 2005/0155133 | A1 * | 7/2005 | Sato | A61B 42/00 |
| | | | | 221/45 |
| 2011/0186589 | A1 * | 8/2011 | Lee | A61B 42/50 |
| | | | | 221/36 |
| 2021/0228299 | A1 * | 7/2021 | Löfholm | A61B 42/50 |
| 2022/0227568 | A1 * | 7/2022 | Brunache | B65D 83/0894 |
| 2025/0017405 | A1 * | 1/2025 | Werth | A47G 25/904 |

FOREIGN PATENT DOCUMENTS

FR 2962314 A1 * 1/2012 ............. A61B 42/40

* cited by examiner

*Primary Examiner* — F Griffin Hall
(74) *Attorney, Agent, or Firm* — Ming Jiang; OPENPTO US LLC

(57) ABSTRACT

The present invention relates to the technical field of glove donning and discloses a glove donning aid machine. The machine comprises a main body provided with an adsorption structure. The adsorption structure grips a glove from a glove box, pulls it downward to detach it, and then opens the cuff into an expanded state oriented downward. A planar rotating structure is also provided on the main body and includes two support arms that move toward or away from each other. When the cuff is opened, the support arms are inserted into the cuff and move apart to expand it. The rotating structure then rotates in a plane to orient the cuff laterally. The structure is simple and enables automated operation for quick glove donning. Since only planar rotation is used, no spatial inversion is required, reducing space occupation and allowing the glove donning aid machine to be easily wall-mounted.

10 Claims, 7 Drawing Sheets

2013

201

2011

2014

400

401

GLOVE DONNING AID MACHINE

TECHNICAL FIELD

The present invention relates to the technical field of glove donning, and more particularly to a glove donning aid machine.

BACKGROUND

In certain environments or specific work scenarios, users are required to wear gloves to meet operational requirements. Most gloves are made of latex material and have an elastic thin-film structure, which allows for elastic deformation.

The interior of the glove defines a donning cavity, which includes finger cavities for accommodating fingers and a palm cavity for accommodating the palm. The end of the glove is provided with a cuff that is in communication with the palm cavity. When donning the glove, the cuff must be expanded or opened first, and the hand must then be slowly inserted into the donning cavity so that the fingers enter the finger cavities and the palm fits into the palm cavity, until the entire hand is positioned inside the glove. This operation is inconvenient and significantly reduces the efficiency of glove donning.

Some glove donning aid machines are commercially available to assist users in wearing gloves. These machines typically use an adsorption mechanism to extract a glove from a glove box and expand the glove's cuff into an open state. A flipping mechanism is then employed to stretch the cuff further into an expanded configuration. The flipping mechanism performs a spatial inversion from the inside out, such that the cuff is turned outward, thereby allowing the user's hand to easily pass through the cuff and into the glove.

However, in existing technologies, the flipping mechanism of the glove donning aid machine requires substantial spatial inversion, which demands a large operating space. As a result, such glove donning aid machines tend to be bulky, have complex structures, and are inconvenient to install and use.

SUMMARY

The objective of the present invention is to provide a glove donning aid machine, which aims to address the problem in the prior art wherein existing glove donning aid machines are inconvenient to install and use.

To achieve the above objective, the present invention provides a glove donning aid machine, comprising a main body mounted on a wall. The main body is provided with a placement area for positioning a glove box, the glove box containing gloves. The main body is further provided with an adsorption structure that grips the gloves inside the glove box. After pulling the gloves downward to detach them from the glove box, the adsorption structure opens the glove cuffs into an expanded state, with the glove cuffs oriented downward relative to the main body.

The main body is further provided with a planar rotating structure located below the adsorption structure. The rotating structure comprises two support arms that move toward or away from each other. When the glove cuff is in an opened state, the two support arms are inserted into the glove cuff from below. The two support arms then move apart to expand the glove cuff, and the rotating structure rotates in a plane to orient the glove cuff laterally relative to the main body.

In a further embodiment, the adsorption structure includes two clamping arms that move toward or away from each other. A clamping gap is defined between the two clamping arms for allowing the glove to pass through. The two clamping arms are positioned below the placement area and are provided with multiple vacuum suction heads made of sticky silicone material.

When a glove from the glove box passes through the clamping gap, the two clamping arms move toward each other, and the vacuum suction heads on the clamping arms adsorb the glove. The two clamping arms clamp and secure the glove, and then pull the glove downward to detach it from the glove box. Subsequently, the two clamping arms move apart, thereby opening the glove cuff into an expanded state.

In a further embodiment, each clamping arm has a clamping surface facing the clamping gap. The clamping surface is recessed to form a recessed area, and the vacuum suction heads are disposed within the recessed area, flush with the clamping surface.

In a further embodiment, the two clamping arms are each provided with a contact point exposed on the clamping surface. When the glove is positioned within the clamping gap and secured by the two clamping arms, the contact points remain electrically disconnected. When the clamping surfaces of the two clamping arms abut each other, the contact points are in contact and form an electrical connection.

In a further embodiment, the main body is provided with an upper moving plate that moves vertically. The two clamping arms are movably connected to the upper moving plate and arranged horizontally in a transverse direction. When the upper moving plate moves upward and the glove passes through the clamping gap, the two clamping arms move toward each other to secure the glove. The upper moving plate then moves downward to pull the glove downward until the glove detaches from the glove box. After detachment, the two clamping arms move apart to open the glove cuff into an expanded state.

In a further embodiment, each of the two clamping arms is connected to an upper rack, and the two upper racks are arranged opposite to each other with a spacing. The upper racks are movably connected to the upper moving plate. An upper gear is arranged between the two upper racks and engages both racks. When the upper gear rotates, it drives the two upper racks to move linearly and synchronously, thereby driving the two clamping arms to move toward or away from each other.

In a further embodiment, the main body is provided with a lower moving plate that moves vertically. A rotating plate that rotates in a plane relative to the lower moving plate is arranged on the lower moving plate. The two support arms are movably connected to the rotating plate. When the glove cuff is opened into an expanded state, the lower moving plate moves upward. The two support arms are inserted into the glove cuff, and then move apart to expand the glove cuff. The rotating plate then rotates in the plane relative to the lower moving plate to orient the glove cuff laterally relative to the main body.

In a further embodiment, each of the two support arms is connected to a lower rack, and the two lower racks are arranged opposite to each other with a spacing. The lower racks are movably connected to the lower moving plate. A lower gear is arranged between the two lower racks and engages both racks. When the lower gear rotates, it drives the two lower racks to move linearly and synchronously, thereby driving the two support arms to move toward or away from each other.

In a further embodiment, the support arms are arranged in a bent shape and include upwardly oriented longitudinal sections. The two longitudinal sections are arranged opposite to each other with a spacing. When the two support arms move toward or away from each other, the two longitudinal sections move toward or away from each other synchronously. When the glove cuff is opened into an expanded state, the two longitudinal sections are inserted into the glove cuff from below. The support arms then move apart, and the longitudinal sections move apart synchronously to expand the glove cuff.

In a further embodiment, each longitudinal section has an outward-facing surface that is arcuately shaped. A rolling shaft is arranged within the longitudinal section and extends along its height direction. The rolling shaft passes through the outward-facing surface and is exposed in the middle of the surface. Raised shafts are arranged at both ends of the outward-facing surface, and extend along the height direction of the longitudinal section. After the longitudinal sections are inserted into the glove cuff, the outward-facing surfaces face the glove. When the longitudinal sections move apart to expand the glove, the glove is supported against the rolling shafts and the raised shafts, forming a gap between the glove and the outward-facing surfaces.

Compared with the prior art, the glove donning aid machine provided by the present invention utilizes an adsorption structure to clamp and secure a glove from a glove box, pulls the glove downward to detach it from the box, and opens the cuff into an expanded state. Then, two support arms of the rotating structure are inserted into the cuff. The support arms move apart to further expand the cuff. The rotating structure then rotates in a plane to orient the glove cuff laterally relative to the main body, allowing the user's hand to pass through the cuff from the side and complete glove donning.

The glove donning aid machine has a simple structure and enables automated operation with smooth execution, allowing gloves to be donned quickly and efficiently. Furthermore, since the rotating structure only performs planar rotation to laterally orient the glove cuff, no spatial inversion is required, minimizing space usage. This facilitates installation and use, and the machine can be directly wall-mounted.

DETAILED DESCRIPTION

Figure 1:
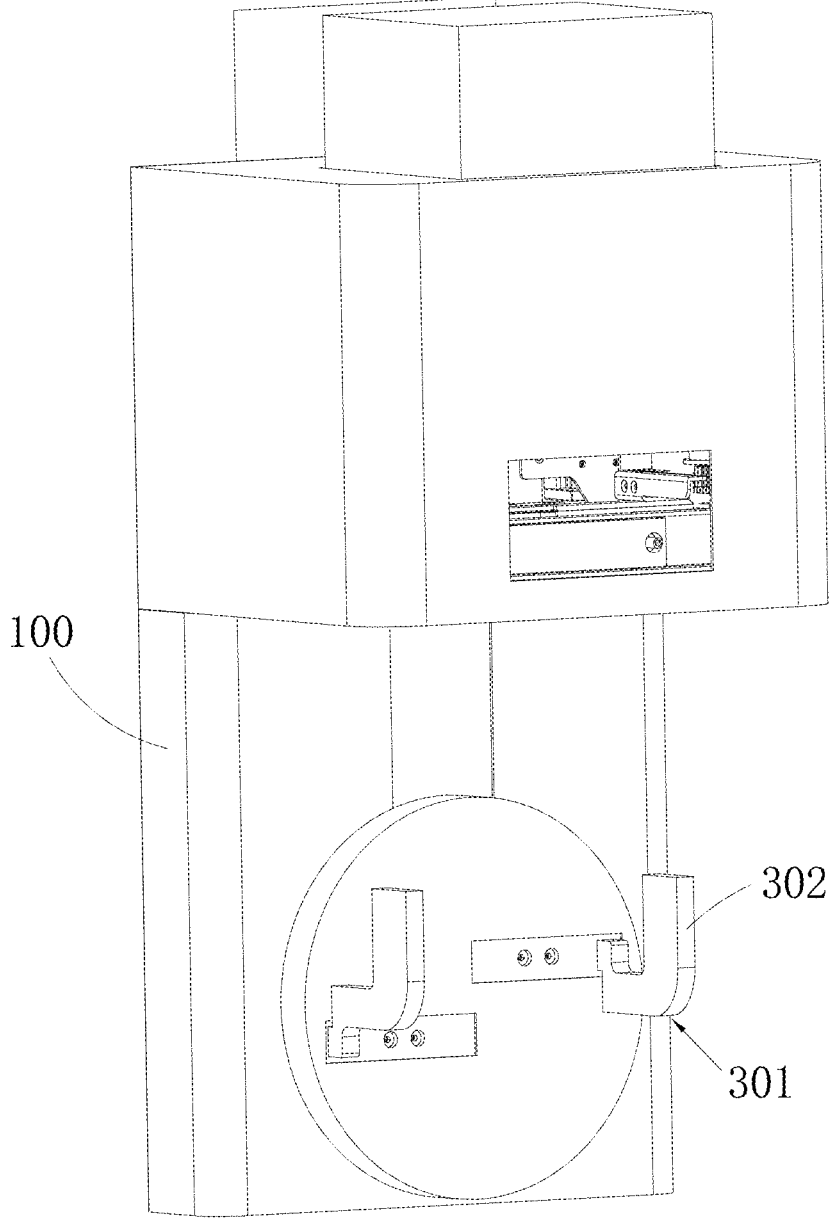
FIG. 1 is a perspective schematic view of the glove donning aid machine provided by the present invention.

To make the objectives, technical solutions, and advantages of the present invention clearer, the following provides a detailed description of the present invention with reference to the accompanying drawings and exemplary embodiments. It should be understood that the specific embodiments described herein are merely illustrative of the invention and are not intended to limit its scope.

The implementation of the present invention will now be described in detail with reference to specific embodiments.

In the drawings of the present embodiment, the same or similar reference numerals denote the same or similar components. In the description of the present invention, it should be understood that terms such as "upper," "lower," "left," "right," and the like indicate orientation or positional relationships based on the figures. These terms are used only for the purpose of describing the invention and simplifying the explanation, and are not intended to indicate or imply that the referenced structures must be constructed or operated in particular orientations. Therefore, positional terms in the figures are illustrative and should not be construed as limiting. Those skilled in the art can understand the meaning of such terms according to the specific context.

Figure 2:
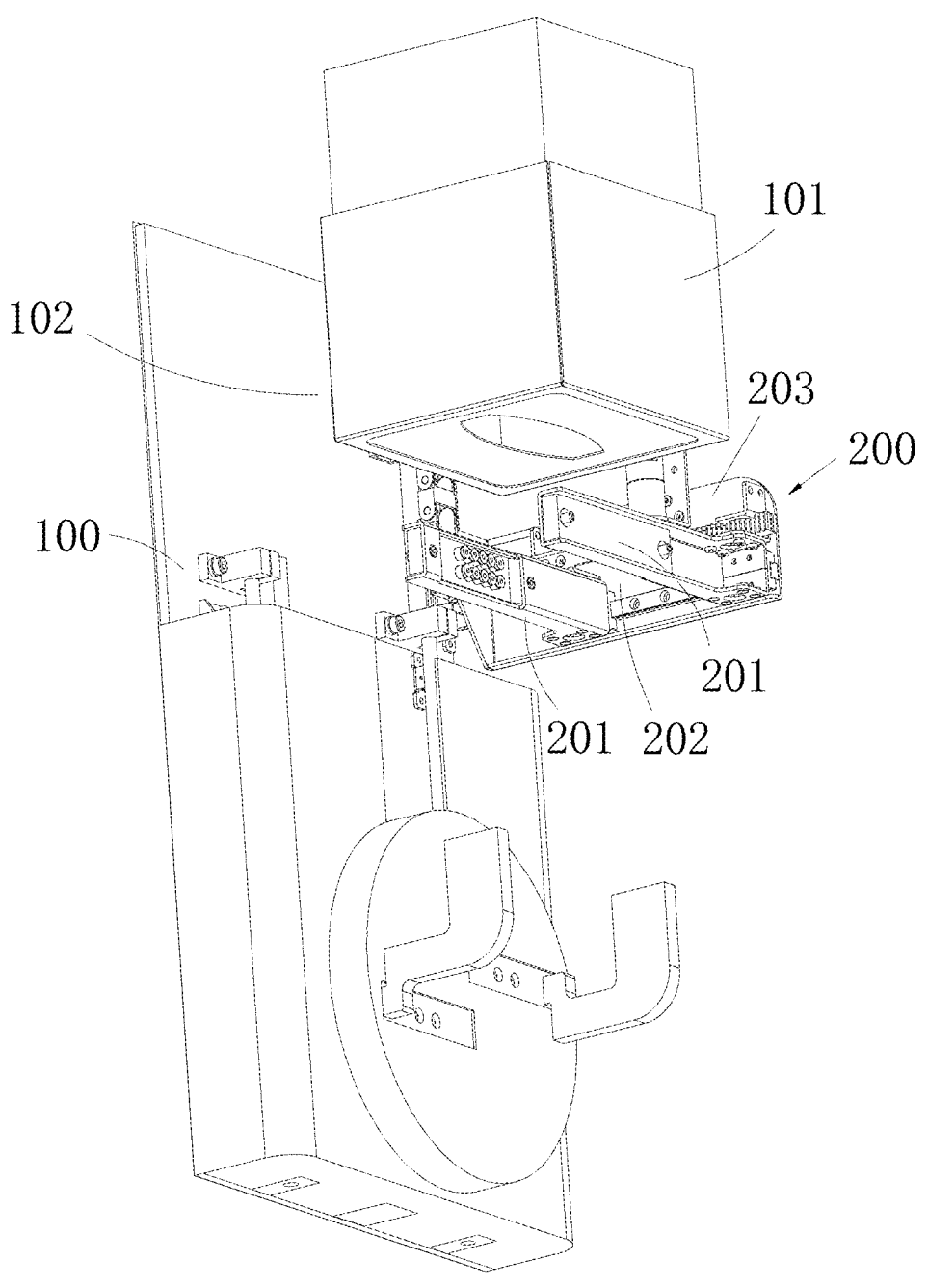
FIG. 2 is a partial perspective schematic view of the glove donning aid machine provided by the present invention.
Figure 3:
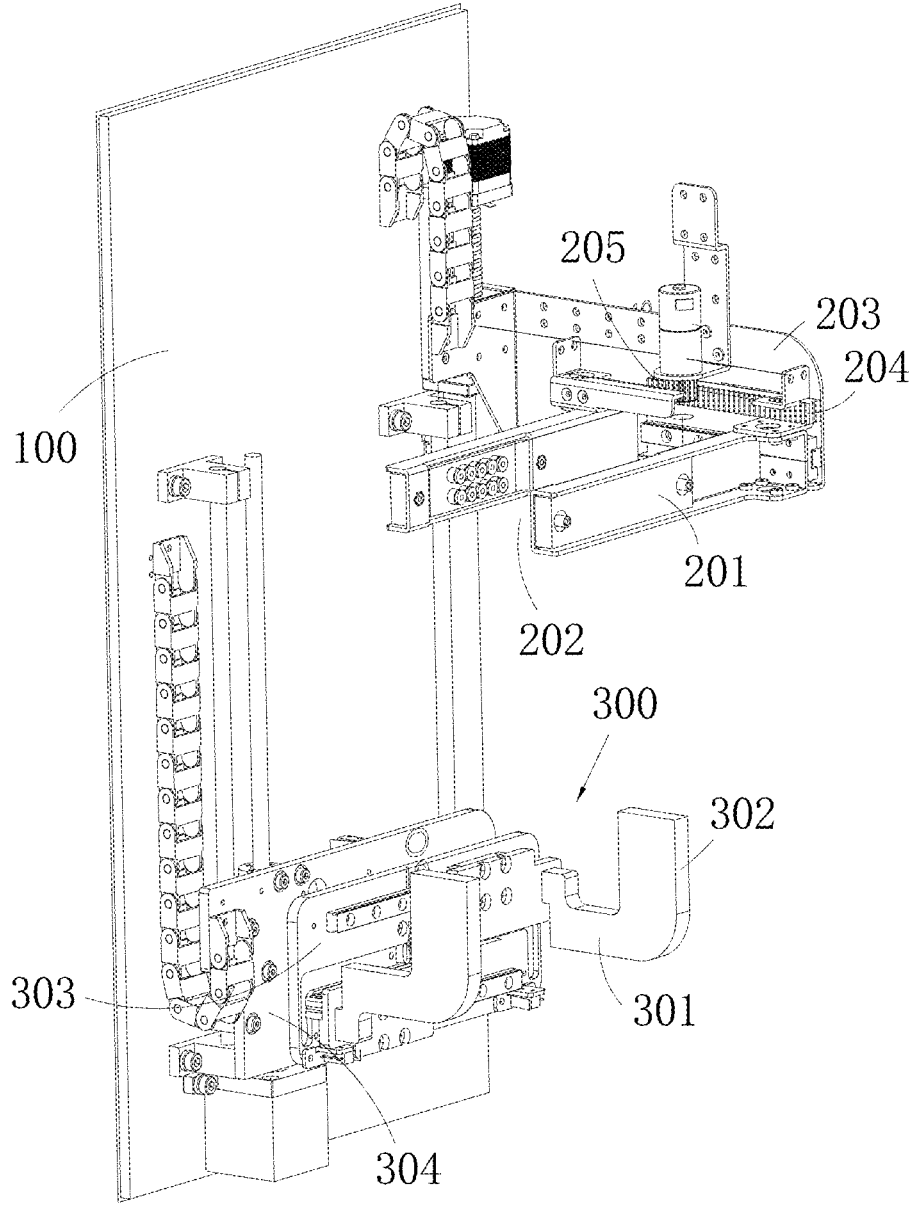
FIG. 3 is another partial perspective schematic view of the glove donning aid machine provided by the present invention.
Figure 4:
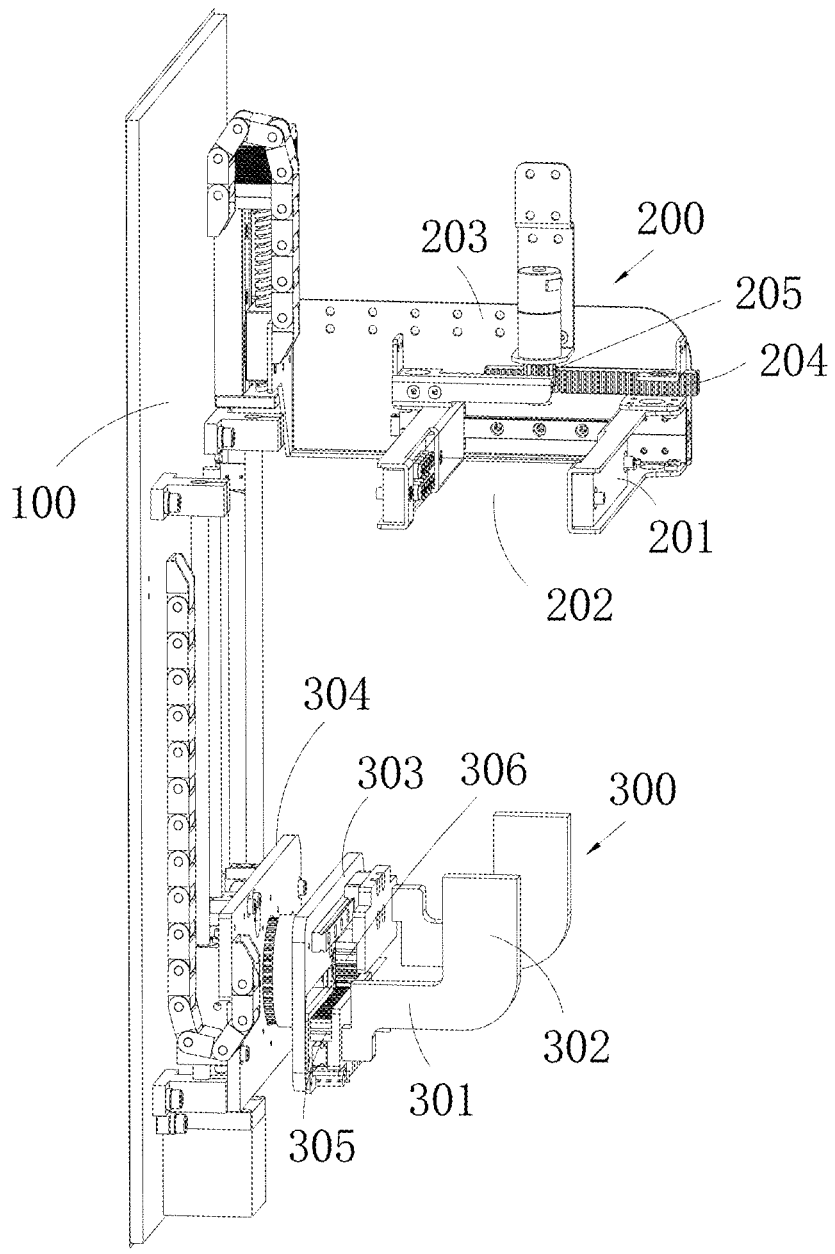
FIG. 4 is yet another partial perspective schematic view of the glove donning aid machine provided by the present invention.
Figure 5:
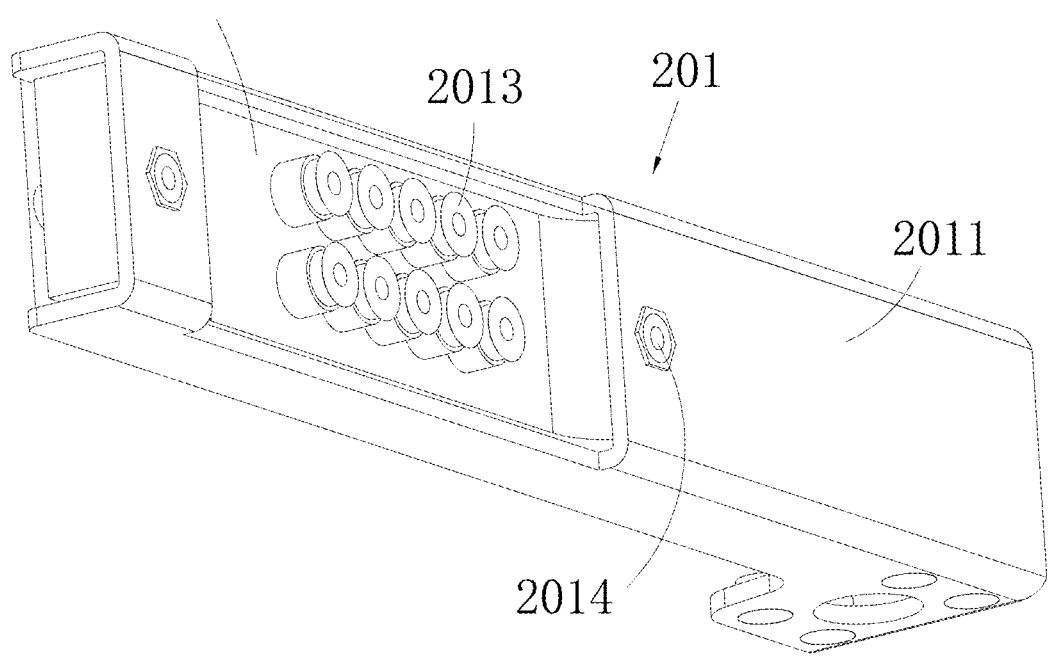
FIG. 5 is a perspective schematic view of the clamping arm provided by the present invention.
Figure 6:
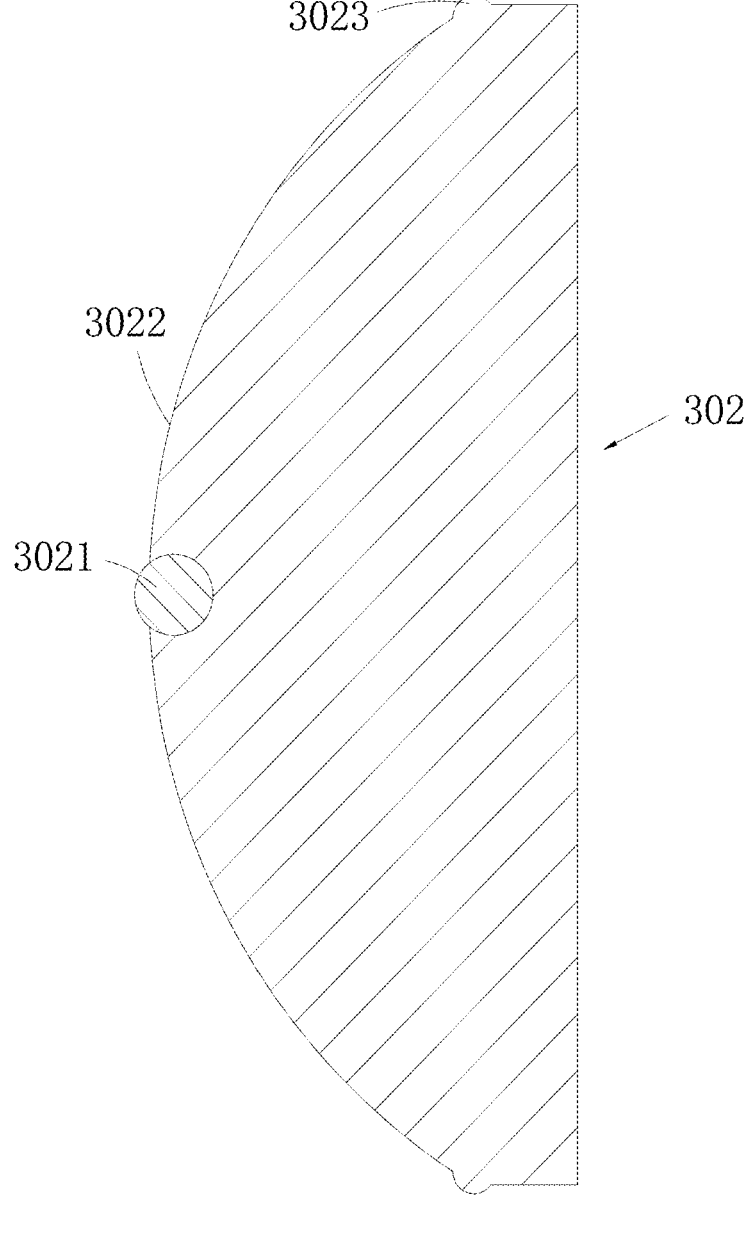
FIG. 6 is a sectional schematic view of the longitudinal section provided by the present invention.
Figure 7:
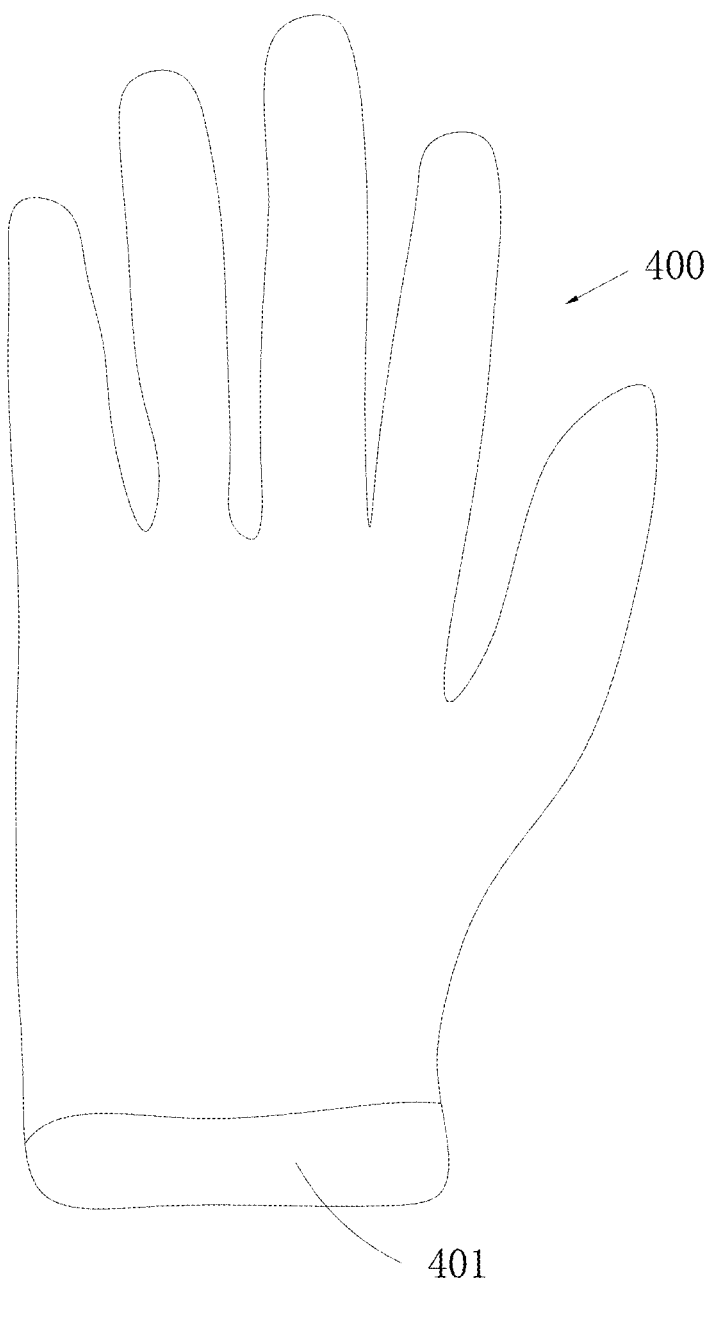
FIG. 7 is a perspective schematic view of the glove provided by the present invention.

With reference to FIGS. 1-7, a preferred embodiment of the glove donning aid machine provided by the present invention is described below.

The glove donning aid machine comprises a main body 100 mounted on a wall and may be installed in a wall-mounted configuration. The main body 100 is provided with a placement area 102 for positioning a glove box 101, which contains gloves 400. Multiple gloves 400 in the glove box 101 are arranged in a folded and stacked manner. When one glove 400 is pulled out from the glove box 101, the cuff 401 of the next glove 400 is exposed below the glove box 101. Once all gloves 400 in the glove box 101 are pulled out, a new glove box 101 can be replaced.

The main body 100 is provided with an adsorption structure 200. The adsorption structure 200 grips a glove 400 inside the glove box 101 and pulls the glove 400 downward to detach it from the glove box 101. Then, the adsorption structure 200 opens the cuff 401 of the glove 400 into an expanded state, with the cuff 401 oriented downward relative to the main body 100.

After the glove 400 is clamped and secured by the adsorption structure 200, it is pulled downward until it detaches from the glove box 101. Thereafter, the cuff 401 of the glove 400 is opened into an expanded state to facilitate the subsequent operation.

The main body 100 is further provided with a rotating structure 300 capable of planar rotation, which is positioned below the adsorption structure 200. The term "planar rotation" as used herein refers to rotation along a trajectory in a single plane.

The rotating structure 300 includes two support arms 301 that move toward or away from each other. When the glove cuff 401 is in an opened state, the two support arms 301 are inserted into the cuff 401 from below. The two support arms 301 then move apart to expand the cuff 401. The rotating structure 300 subsequently performs planar rotation to orient the cuff 401 laterally relative to the main body 100.

In the glove donning aid machine provided above, the adsorption structure 200 clamps and secures a glove 400 in the glove box 101, pulls the glove 400 downward to detach it from the glove box 101, and opens the cuff 401 into an expanded state. Then, the two support arms 301 of the rotating structure 300 are inserted into the cuff 401. The support arms 301 move apart to further expand the cuff 401. The rotating structure 300 then rotates in a plane to orient the cuff 401 laterally relative to the main body 100, so that the user's hand can laterally pass through the cuff 401 into the glove 400, completing the donning of the glove 400.

The glove donning aid machine features a simple structure, enabling automated operation and smooth performance, which facilitates rapid and efficient glove donning. Furthermore, since the rotating structure 300 only performs planar rotation, the cuff 401 of the glove 400 can be oriented laterally without requiring spatial inversion, thereby minimizing space requirements. This makes the glove donning aid machine easy to install and use, and it can be mounted directly on a wall.

In this embodiment, the adsorption structure 200 includes two clamping arms 201 configured to move toward or away from each other. A clamping gap 202 is defined between the two clamping arms 201, allowing a glove 400 to pass through. The two clamping arms 201 are located below the placement area 102. Multiple vacuum suction heads 2013 are arranged on the clamping arms 201, and the vacuum suction heads 2013 are made of tacky silicone material.

The two clamping arms 201 are arranged opposite to each other. When the clamping arms 201 move away from each other, the clamping gap 202 increases. When the clamping arms 201 move toward each other, the clamping gap 202 decreases. When a glove 400 passes through the clamping gap 202, the two clamping arms 201 move toward each other to clamp and fix the glove 400. At this time, the vacuum suction heads 2013 simultaneously adsorb the glove 400. The suction heads 2013 themselves have a certain tackiness, which enhances the adhesion to the glove 400 during clamping. When the clamping arms 201 move apart, the vacuum suction heads 2013 provide sufficient suction force to ensure that the glove cuff 401 is opened into an expanded state.

As the clamping arms 201 move apart, the vacuum suction heads 2013 continue to adsorb the glove 400. With the increase in the clamping gap 202, the glove cuff 401 is gradually opened until a predetermined width is reached, placing the glove 400 in an expanded state.

Once the support arms 301 are inserted into the cuff 401 and the glove 400 is expanded into the open state, the glove 400 becomes fixed on the two support arms 301. At this point, the vacuum suction heads 2013 may disengage from the glove 400, thereby releasing the glove 400 from the clamping arms 201.

When a glove 400 passes through the clamping gap 202 from the glove box 101, the two clamping arms 201 move toward each other. The vacuum suction heads 2013 on the clamping arms 201 adsorb the glove 400. The two clamping arms 201 clamp and secure the glove 400, and pull the glove 400 downward to detach it from the glove box 101. Then, the two clamping arms 201 move away from each other to open the glove cuff 401 into an expanded state.

By clamping and fixing the glove 400 with the two clamping arms 201, the glove 400 can be pulled out of the glove box 101. Meanwhile, the clamping arms 201 also adsorb the glove 400, facilitating subsequent expansion of the glove 400. The structure is simple, supports automated and continuous operation, and significantly improves operational efficiency.

In this embodiment, each clamping arm 201 has a clamping surface 2011 facing the clamping gap 202. The clamping surface 2011 is recessed to form a recessed area 2012. Multiple vacuum suction heads 2013 are arranged within the recessed area 2012 and are flush with the clamping surface 2011. The recessed area 2012 facilitates the arrangement of the vacuum suction heads 2013. Since the suction heads 2013 are flush with the clamping surface 2011, when the two clamping arms 201 move toward each other to clamp the glove 400, the clamping surfaces 2011 press against the glove 400 while the suction heads 2013 contact and adsorb the glove 400 to secure it in place.

In this embodiment, each of the two clamping arms 201 is provided with a contact 2014, which is exposed on the clamping surface 2011. When the glove 400 is positioned within the clamping gap 202 and the clamping arms 201 clamp and secure the glove 400, the two contacts 2014 remain separated and electrically disconnected. When the clamping surfaces 2011 of the two clamping arms 201 abut each other, the two contacts 2014 come into contact and form an electrical connection.

Therefore, when the two clamping arms 201 move toward each other to clamp, the state of the contacts 2014—whether connected or disconnected—can be used to determine whether a glove 400 has been clamped and fixed. This, in turn, allows the system to determine whether a glove 400 is present in the glove box 101 and whether the glove box 101 needs to be replaced.

The connection or disconnection signal of the two contacts 2014 can be transmitted to a controller, which may be a circuit board arranged on the main body 100. The controller determines whether a glove 400 has been clamped based on the signal. It may further determine the presence of gloves 400 in the glove box 101 and may indicate the status through indicator lights or voice prompts.

In this embodiment, an infrared sensor is provided on the main body 100. The infrared sensor is electrically connected to the controller, via wired or wireless communication. When a user intends to don a glove 400, the user may block the infrared sensor. Upon detecting the signal, the infrared sensor sends it to the controller, which then initiates operation of the glove donning aid machine.

In this embodiment, the main body 100 is provided with an upper moving plate 203 that moves vertically. The two clamping arms 201 are movably connected to the upper moving plate 203 and are arranged horizontally in a transverse direction. When the upper moving plate 203 moves upward and a glove 400 from the glove box 101 passes through the clamping gap 202, the two clamping arms 201 move toward each other to clamp and secure the glove 400. Afterward, the upper moving plate 203 moves downward, pulling the glove 400 downward until it detaches from the glove box 101. Once the glove 400 is detached, the two clamping arms 201 move away from each other, opening the glove cuff 401 into an expanded state.

Through the vertical movement of the upper moving plate 203, the two clamping arms 201 are synchronously driven to move upward or downward. When the clamping arms 201 move upward with the upper moving plate 203, they clamp and secure the glove 400 positioned in the clamping gap 202. When the clamping arms 201 are holding the glove 400 and the upper moving plate 203 moves downward, the glove 400 is pulled out of the glove box 101.

In this embodiment, the two clamping arms 201 are respectively connected to upper racks 204, which are arranged opposite each other with a spacing. The upper racks 204 are movably connected to the upper moving plate 203. An upper gear 205 is arranged between the two upper racks 204 and engages both racks. When the upper gear 205 rotates, it drives the two upper racks 204 to move linearly and synchronously, thereby driving the two clamping arms 201 to move toward or away from each other.

Accordingly, when the upper gear 205 rotates, it synchronously drives the linear movement of the two upper racks 204. The linear displacement between the two upper racks 204 results in the movement of the two clamping arms 201 either toward or away from each other. This structure is simple and facilitates the synchronized movement of the two clamping arms 201.

In this embodiment, the main body 100 is further provided with a lower moving plate 304 that moves vertically. A rotating plate 303, capable of planar rotation relative to the lower moving plate 304, is mounted thereon. The two support arms 301 are movably connected to the rotating plate 303. When the glove cuff 401 is opened into an expanded state, the lower moving plate moves upward, and the two support arms 301 are inserted into the cuff 401. The support arms 301 then move apart to expand the cuff 401. Subsequently, the rotating plate 303 rotates in a plane relative to the lower moving plate 304, thereby orienting the glove cuff 401 laterally with respect to the main body 100.

The vertical movement of the lower moving plate 304 synchronously drives the upward or downward movement of the rotating plate 303 and the two support arms 301. When the lower moving plate 304 moves upward, the rotating plate 303 and the two support arms 301 move upward together. The two support arms 301 are inserted into the already opened cuff 401. At this point, the support arms 301 move apart to expand the cuff 401. The vacuum suction heads 2013 on the clamping arms 201 disengage from the glove 400, so the glove 400 is released from the clamping arms 201 and is now supported and fixed by the two support arms 301.

When the two support arms 301 support the glove 400 and the lower moving plate 304 moves downward, the rotating plate 303 performs planar rotation to orient the glove cuff 401 laterally relative to the main body 100. In this position, the user's hand may approach from the lateral side of the main body 100 and insert through the expanded cuff 401. Once the glove 400 is fully donned onto the user's hand, the two support arms 301 move toward each other while the user's hand synchronously pulls the glove 400 forward. The glove 400 eventually detaches from the support arms 301, and the glove donning aid machine returns to its initial state in preparation for the next cycle.

In this embodiment, each of the two support arms 301 is connected to a lower rack 305, and the two lower racks 305 are arranged opposite each other with a spacing. The lower racks 305 are movably connected to the lower moving plate 304. A lower gear 306 is arranged between the two lower racks 305 and engages both racks. When the lower gear 306 rotates, it drives the two lower racks 305 to move linearly and synchronously, thereby driving the two support arms 301 to move toward or away from each other.

By rotating the lower gear 306, the two lower racks 305 are driven to move linearly and synchronously, either toward each other or away from each other, depending on the rotation direction of the lower gear 306. The structure is simple and facilitates the synchronized movement of the two support arms 301.

In this embodiment, each support arm 301 is arranged in a bent shape and includes an upwardly oriented longitudinal section 302. The two longitudinal sections 302 of the support arms 301 are spaced apart and face each other. When the two support arms 301 move toward or away from each other, the two longitudinal sections 302 move synchronously toward or away from each other.

When the glove cuff 401 is opened into an expanded state, the two longitudinal sections 302 are inserted into the cuff 401 from below. The support arms 301 then move away from each other, causing the longitudinal sections 302 to also move apart and thereby expand the glove cuff 401.

The support arms 301 are configured to form longitudinal sections 302 in a synchronized manner. This facilitates insertion of the longitudinal sections 302 into the glove cuff 401 from below. Once the two longitudinal sections 302 expand the cuff 401, the user's hand can be inserted into the glove 400. As the glove 400 is worn onto the user's hand and the hand continues to move forward, the glove 400 detaches from the longitudinal sections 302.

In this embodiment, each longitudinal section 302 includes an outward-facing surface 3022, which is arranged in an arcuate shape. A rolling shaft 3021 is rotatably disposed within the longitudinal section 302 and extends along its height direction. The rolling shaft 3021 passes through the outward-facing surface 3022 and is exposed at the center of the outward-facing surface 3022.

Raised shafts 3023 are respectively disposed at both ends of the outward-facing surface 3022 and extend along the height direction of the longitudinal section 302. When the longitudinal sections 302 are inserted into the glove cuff 401, the outward-facing surfaces 3022 are oriented toward the glove 400. As the two longitudinal sections 302 move away from each other to expand the glove 400, the glove 400 comes into contact with the rolling shaft 3021 and the raised shafts 3023, and a gap is maintained between the glove 400 and the outward-facing surface 3022.

The foregoing description is merely a preferred embodiment of the present invention and is not intended to limit the scope of the invention. Any modifications, equivalent replacements, or improvements made within the spirit and principle of the present invention shall be encompassed within the scope of protection of the present invention.

The invention claimed is:

1. A glove donning aid machine, comprising a main body configured for being mounted on a wall, the main body being provided with a placement area for positioning a glove box, the glove box containing gloves;

an adsorption structure disposed on the main body, the adsorption structure being configured to grip a glove from the glove box and pull the glove downward to detach it from the glove box, and to open a cuff of the glove into an expanded state, the cuff being oriented downward relative to the main body;

a planar rotating structure disposed on the main body and located below the adsorption structure, the rotating structure comprising two support arms configured to move toward or away from each other;

wherein, when the cuff is in the expanded state, the two support arms are inserted into the cuff from below, then move away from each other to further expand the cuff, and the rotating structure rotates in a plane to orient the cuff laterally relative to the main body.

2. The glove donning aid machine of claim 1, wherein the adsorption structure comprises two clamping arms configured to move toward or away from each other, a clamping gap is defined between the two clamping arms for allowing the glove to pass through, the clamping arms being located below the placement area, each of the clamping arms being provided with a plurality of vacuum suction heads made of tacky silicone material;

wherein, after the glove passes through the clamping gap, the two clamping arms move toward each other to clamp the glove, the vacuum suction heads adsorbing the glove; and after the glove is pulled downward to detach from the glove box, the two clamping arms move away from each other to open the cuff into the expanded state.

3. The glove donning aid machine of claim 2, wherein each clamping arm has a clamping surface facing the clamping gap, the clamping surface being recessed to form a recessed area, and the plurality of vacuum suction heads being arranged within the recessed area and flush with the clamping surface.

4. The glove donning aid machine of claim 3, wherein each of the two clamping arms is provided with a contact point exposed on the clamping surface;

wherein, when the glove is clamped between the two clamping arms, the contact points are electrically disconnected; and when the clamping surfaces of the two clamping arms abut each other, the contact points make electrical contact with each other.

5. The glove donning aid machine of claim 2, wherein the main body is provided with an upper moving plate configured to move vertically, the two clamping arms being movably connected to the upper moving plate and arranged horizontally in a transverse direction;

wherein, when the upper moving plate moves upward and the glove passes through the clamping gap, the two clamping arms move toward each other to clamp the glove, then the upper moving plate moves downward to pull the glove downward until it detaches from the glove box; and after the glove is detached, the two clamping arms move away from each other to open the cuff into the expanded state.

6. The glove donning aid machine of claim 5, wherein each of the two clamping arms is connected to an upper rack, the two upper racks being arranged opposite each other with a spacing and movably connected to the upper moving plate;

an upper gear is disposed between the two upper racks and engaged with both, and rotation of the upper gear drives the two upper racks to move linearly and synchronously, thereby driving the clamping arms to move toward or away from each other.

7. The glove donning aid machine of claim 6, wherein the main body is provided with a lower moving plate configured to move vertically, a rotating plate rotatable in a plane relative to the lower moving plate is disposed on the lower moving plate, and the two support arms are movably connected to the rotating plate;

wherein, when the cuff is opened into the expanded state, the lower moving plate moves upward, the support arms are inserted into the cuff and then move away from each other to expand the cuff, and the rotating plate rotates in a plane to orient the cuff laterally relative to the main body.

8. The glove donning aid machine of claim 7, wherein each of the two support arms is connected to a lower rack, the two lower racks being arranged opposite each other with a spacing and movably connected to the lower moving plate;

a lower gear is disposed between the two lower racks and engaged with both, and rotation of the lower gear drives the two lower racks to move linearly and synchronously, thereby driving the support arms to move toward or away from each other.

9. The glove donning aid machine of claim 7, wherein each support arm is bent and includes a longitudinal section extending upward, the two longitudinal sections being arranged opposite each other with a spacing;

wherein, when the support arms move toward or away from each other, the two longitudinal sections move synchronously; and when the cuff is opened into the expanded state, the two longitudinal sections are inserted into the cuff from below and then move away from each other to expand the cuff.

10. The glove donning aid machine of claim 9, wherein each longitudinal section has an outward-facing surface arranged in an arcuate shape, a rolling shaft is rotatably disposed within the longitudinal section and extends in a height direction thereof, the rolling shaft passes through the outward-facing surface and is exposed at a central position thereof;

raised shafts are disposed at both ends of the outward-facing surface and extend in the height direction of the longitudinal section;

wherein, when the longitudinal sections are inserted into the cuff and move apart to expand the glove, the glove contacts the rolling shaft and the raised shafts, and a gap is formed between the glove and the outward-facing surface.

\* \* \* \* \*